United States Patent
Andersson et al.

(10) Patent No.: US 6,676,959 B1
(45) Date of Patent: Jan. 13, 2004

(54) NICOTINE-CONTAINING PHARMACEUTICAL COMPOSITIONS GIVING A RAPID TRANSMUCOSAL ABSORPTION

(75) Inventors: Sven Börje Andersson, Ödåkra (SE); Tomas Landh, Lund (SE); Stefan Jonn, Helsingborg (SE); Stefan Grudén, Rydebäck (SE); Nils-Olof Lindberg, Malmö (SE)

(73) Assignee: Pharmacia AB, Helsingborg (SE)

( * ) Notice: Subject to any disclaimer, the term of this patent is extended or adjusted under 35 U.S.C. 154(b) by 0 days.

(21) Appl. No.: 09/856,522

(22) PCT Filed: Nov. 4, 1999

(86) PCT No.: PCT/SE99/01983

§ 371 (c)(1),
(2), (4) Date: Jul. 11, 2001

(87) PCT Pub. No.: WO00/30641

PCT Pub. Date: Jun. 2, 2000

(30) Foreign Application Priority Data

Nov. 23, 1998 (SE) ............................................. 9803986

(51) Int. Cl.[7] ................................................ A61F 13/00
(52) U.S. Cl. ...................... 424/435; 424/434; 424/449; 514/343
(58) Field of Search ................................. 424/434, 435, 424/449; 514/343

(56) References Cited

U.S. PATENT DOCUMENTS 5,362,496 A * 11/1994 Baker et al. ................. 424/434
5,512,306 A    4/1996 Carlsson et al.
5,662,920 A    9/1997 Santus
5,783,207 A    7/1998 Stanley et al.
6,197,827 B1 * 3/2001 Cary ........................... 514/646

FOREIGN PATENT DOCUMENTS

WO   WO 90/03776   4/1990

OTHER PUBLICATIONS

Cook, James W.; Acyl Lactylate Index, *Cosmetics & Toiletries*; vol. 112, No. 10 (1997).
Acme–Hardesty Chemicals–Surfactants Product List, Chemicals & Surfactants; acme–hardesty.com (2002).
Kiwi Web Chemistry & New Zealland; Detergent Chemistry, (2002).
The European Parliament and the Council of the European Union; Directive 2000/36/EC of the European Parliament and of the Council of Jun. 23, 2000; *Official Journal of European Communities*, pp. 19–25., (2000).
Bernard W. Minifie; Chocolate, Cocoa and Confectionery: Science and Technology, Second Edition, Avi Publishing Company, Westport, CT. pp. 79–88.
Beckett, S.T. Industrial Chocolate Manufacture and Use. Second Edition, pp. 241–257.

* cited by examiner

*Primary Examiner*—Jyothsna A Venkat
(74) *Attorney, Agent, or Firm*—Fulbright & Jaworski, LLP

(57) ABSTRACT

Formulations of nicotine for use in nicotine replacement therapy. The formulations are intended for application in the oral cavity where upon the uptake of nicotine mainly takes place through the buccal mucosa. The formulations essentially comprise apolar, polar and surface-active components. The formulations may be administered in combination with other nicotine formulations.

89 Claims, 3 Drawing Sheets

Figure 1:
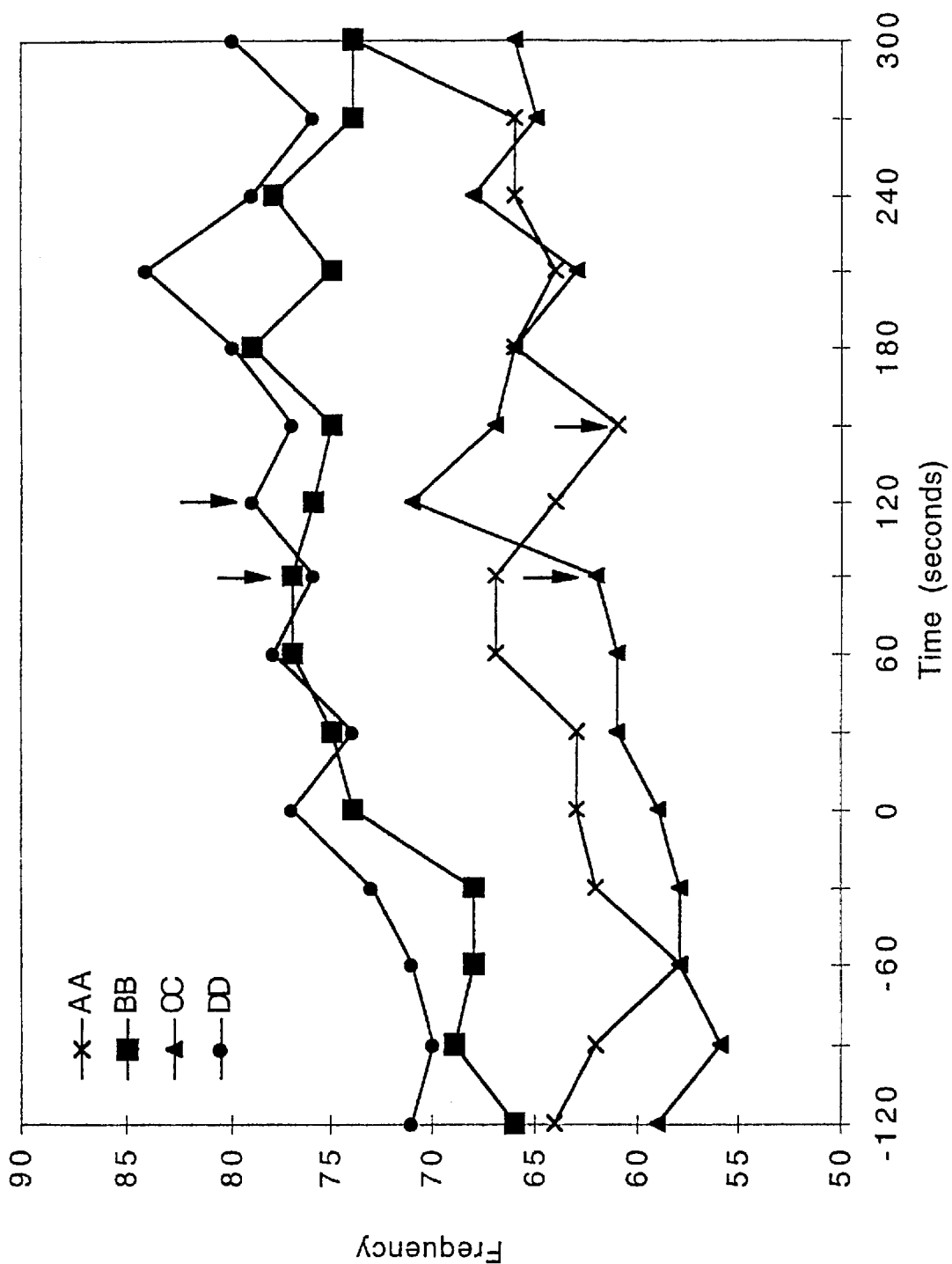

NICOTINE-CONTAINING PHARMACEUTICAL COMPOSITIONS GIVING A RAPID TRANSMUCOSAL ABSORPTION

This application is a U.S. National Stage of International Application No. PCT/SE99/01983, which was filed on Nov. 4, 1999 and claims priority to Swedish Application No. 9803986-0, which was filed on Nov. 23, 1998.

FIELD OF THE INVENTION

This invention relates to compositions comprising nicotine and methods for preparing said compositions being useful in drug therapy, preferably nicotine replacement, including tobacco substitution and smoking cessation.

BACKGROUND AND PRIOR ART

Nicotine replacement therapy as a smoking cessation strategy has been successful in the past. Previous nicotine-containing compositions aiming towards the purpose of reducing nicotine craving for subjects wishing to stop their use of tobacco products include e.g. U.S. Pat. No. 3,845,217 disclosing chewable compositions, U.S. Pat. No. 4,579,858 disclosing high-viscous nicotine nose-drop compositions, U.S. Pat. No. 5,525,351 disclosing nicotine-containing saliva-soluble gels, U.S. Pat. No. 5,656,255 disclosing low-viscous nicotine-containing compositions suitable for nasal spray administration, U.S. Pat. Nos. 4,920,989 and 4,953,572 disclosing the use of inhalation aerosol, BP 1,528,391 and BP 2,030,862 disclosing liquid aerosol formulations adapted as mouth-sprays, and devices for transdermal delivery of nicotine.

A well-known side effect of nicotine is related to its concentration dependent local irritation. This adverse effect is particularly noticeable when nicotine formulations are applied topically, including the transmucosal, comprising buccal and nasal, and transdermal administration routes.

UK Patent application GB 2 230 439 A describes nicotine lozenges with a shell or coating containing an oral-acting local analgesic, preferably eugenol. Though not stated explicitly to be the cause of the so included local analgesic, the aforesaid disclosure is said to substantially ameliorate the sensation of burning in the mouth experienced with conventional nicotine lozenges. Similarly, nicotine-compositions formulated in lozenges containing local analgesic have been disclosed in AU 662877 in which the latter agent is said to temporarily interfere with taste receptors which is said to reduce the desire to eat.

The concentration of nicotine in several of the above mentioned inventions, and product designs thereof, is hence limited by adverse effects caused by or related to its local irritation.

Prior art describes other capsules, tablets, and lozenges for oral delivery of nicotine. For example, WO 88/03803 discloses a chewable capsule filled with a liquid containing 0.1–10.0 mg of nicotine, together with additives for improving flavor and dispersion. The capsules are provided in a variety of pH values to allow the patient a choice of nicotine absorption rates, and are especially intended as an aid to quit smoking.

Another nicotine capsule formulation is disclosed by Jarvik et al. (*Clin. Pharm. Ther.* 1970, 11, 574) for ingestion as a smoking cessation aid. The subjects, according to the theory that intestinal absorption of nicotine could produce significant blood levels, however, apparently swallowed these capsules whole. The study showed a small but significant decrease in the number of cigarettes smoked by subjects, but no quantitative measurements of nicotine blood levels were obtained.

BE 899037 discloses a tablet containing 0.1 to 5 mg nicotine as a base or water-soluble acid salt as an aid for quitting smoking.

Shaw (for example in GB 2 142 822 and U.S. Pat. No. 4,806,356) describes a nicotine lozenge prepared from a mixture of inert filler material, a binder, and either pure nicotine or a nicotine-containing substance by cold compression.

U.S. Pat. No. 5,512,306 discloses a nicotine product for oral delivery in the form of an inclusion complex of nicotine and a cyclodextrin compound. It also discusses the use of various excipients and direct compression for manufacture of the product.

WO 90/03776 discloses nicotine-containing tablets comprising more than 75% PEG. WHO has stated the acceptable daily intake (ADI) of PEG to be 10 mg/kg body weight. Using nicotine tablets according to WO 90/03776 in smoking cessation therapy would though result in an ADI of PEG much higher than 10 mg/kg body weight. Our present invention does not contain PEG at all.

WO 97/42941 discloses a slowly erodible nicotine lozenge that allows delivery to the buccal mucosa over an extended period of time.

The literature also describes different designs of tablets for delivering nicotine to the mouth and digestive system.

Wesnes and Warburton (*Psychopharmacology* 1984, 82, 147; ibid. 1986, 89, 55) discuss the use of nicotine containing dextrose and magnesium hydroxide tablets. The subjects were instructed to keep the tablets in the mouth for some minutes before swallowing, in order to maximize contact with the buccal mucosa.

Several products based on the above mentioned patents are now marketed on an international scale. In addition, several nicotine lozenges are available as over-the-counter products in the U.K. "Resolution" lozenges, manufactured by Phoenix Pharmaceuticals and distributed by Ernest Jackson, contain 0.5 mg nicotine, together with the antioxidant vitamins A, C, and E. "Stoppers" lozenges, distributed by Charwell Pharmaceuticals Ltd., contain 0.5 mg nicotine and are available in chocolate, orange and peppermint flavors.

There are, however, subjects who may have cravings for higher doses of nicotine than those acceptable in applications of prior art and subjects that may not experience a decrease in other withdrawal symptoms because of unsatisfactory nicotine absorption. Furthermore, it has to date been difficult to deliver nicotine in a profile mimicking the nicotine blood levels achieved by consistent smoking, to satisfy cravings for nicotine in people who are attempting to quit smoking, and thus, to provide greater protection against relapse than nicotine replacement therapies is possible with hitherto known. Thus, absorption of nicotine in the use of currently marketed products and as disclosed in prior art of nicotine replacement therapies is not satisfactorily resembling the use of tobacco products, in particular smoking. With chewing gum nicotine replacement therapy for smoking cessation blood peak levels of nicotine is reached after 30 min. with venous blood nicotine levels about ⅓ to ⅔ of the levels attained when smoking (*Br. Med. J.* 1976, 1, 1043). A smoker will usually reach peak blood levels of nicotine 5–10 min. after starting smoking. It is therefore desirable to provide improved compositions and methods which avoid the disadvantages of these conventional nicotine delivery devices and methods while providing an effective means for delivering nicotine for smoking cessation treatment, for reducing nicotine craving, and for treating other conditions responsive to nicotine therapy.

We have surprisingly found that a rapid buccal absorption of nicotine is achieved through the use of nicotine containing formulations based on heterogeneous apolar-polar components. No similar formulations have been disclosed hitherto. The present formulations do not contain polyethylen glycols.

SUMMARY OF THE INVENTION

Compositions for the therapeutic delivery of nicotine are provided. Said compositions comprising nicotine provide rapid transmucosal absorption of nicotine. The compositions are preferably used for therapeutic administration of nicotine. The compositions are, preferably, applicable to, but not restricted to the buccal administration route.

The meaning of "disintegration" as used in the description and in the claims denotes melting, solubilization, erosion or a combinatorial effect of these physical changes of the invention.

The meaning of "melting point range" as used in the description and in the claims refers to the gradual decrease of the amount of solid, semisolid or amorphous material, as opposed to liquid material, as the temperature is increased.

The meaning of increase in "frequency", as measured as the heart beat frequency (rate), as an indirect measure of nicotine absorption is used in the description and in the claims as detailed by Armitage ("Blood levels of nicotine and cotinine attained during smoking" in: *The Workshop on Nicotine,* Nov. 11–13, 1974, Stockholm, Sweden) and Schievelbein ("Nicotine, Resorption and Fate" in *Intl. Encyclop. Pharmacol. Therapeut.* 1984, 114, 1). These references show that a rapid increase in plasma nicotine levels is associated with an increase in arterial blood pressure and heart rate.

"Adhesiveness" is readily appreciated, by those skilled in the art, to be a consequence of the behavior of the formulation in question in the environment of the site of application with which it is striving to approach uniformity in the sense of thermodynamics and mass transport. Adhesiveness is achieved through the driving force to reach close apposition caused by the formulation's thermodynamic degree of freedom followed by the establishment of non-covalent interaction to the surface or site of application.

LEGENDS TO THE FIGURES

FIG. 1 shows the influence of application of a buccal tablet according to Example 4 on the heart beat frequency (rate) of four individuals (AA, BB, CC, and DD) as a function of time. Time –120—0 represents time prior to application of the dosage form. At time 0 individuals applied the buccal tablet according to the test protocol. Arrows indicate the time at which the tablet had disintegrated as reported by each individual.

Figure 2:
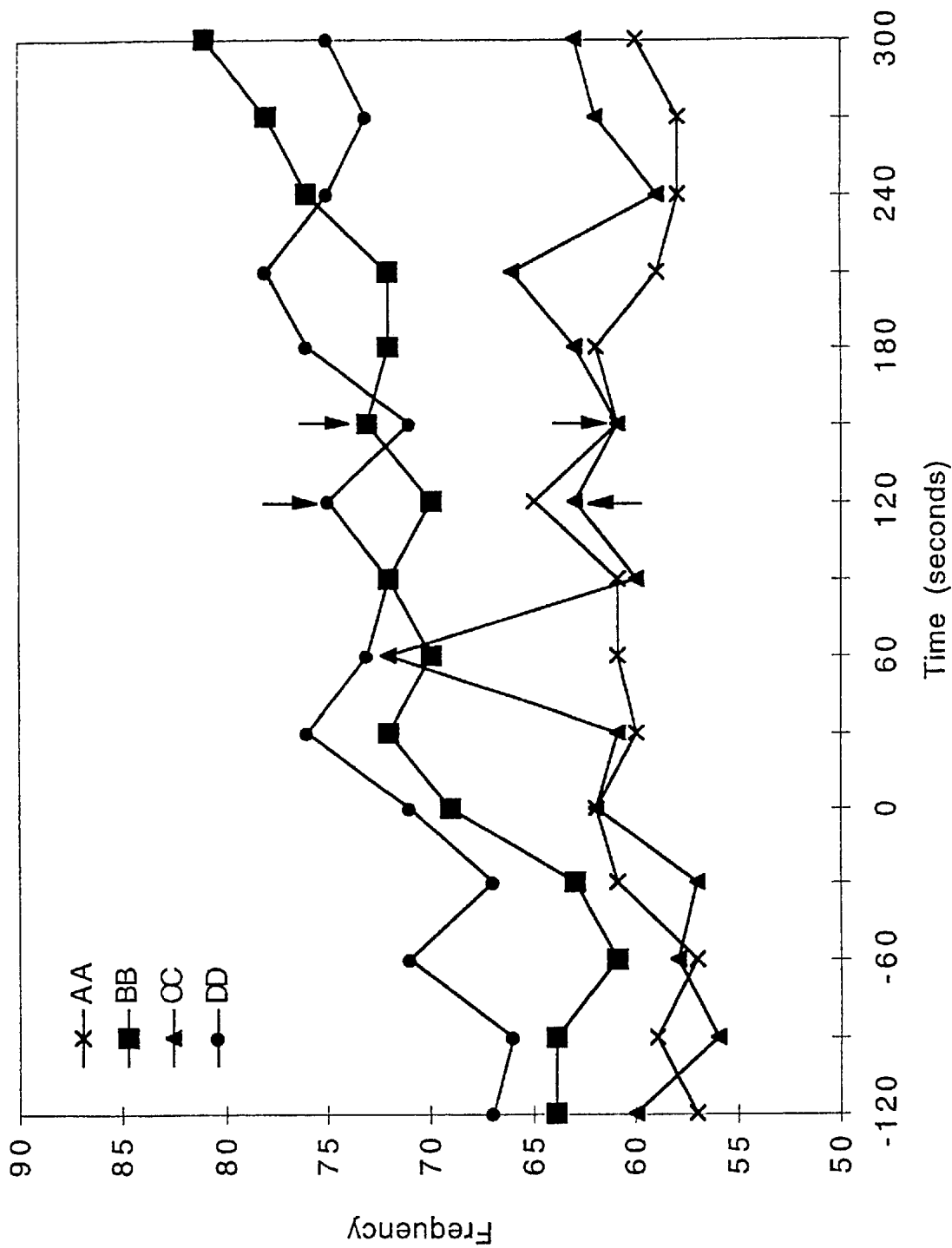

FIG. 2 shows the influence of application of a buccal tablet according to Example 5 on the heart beat frequency (rate) of four individuals (AA, BB, CC, and DD) as a function of time. Time –120—0 represents time prior to application of the dosage form. At time 0 individuals applied the buccal tablet according to the test protocol. Arrows indicate the time at which the tablet had disintegrated as reported by each individual.

Figure 3:
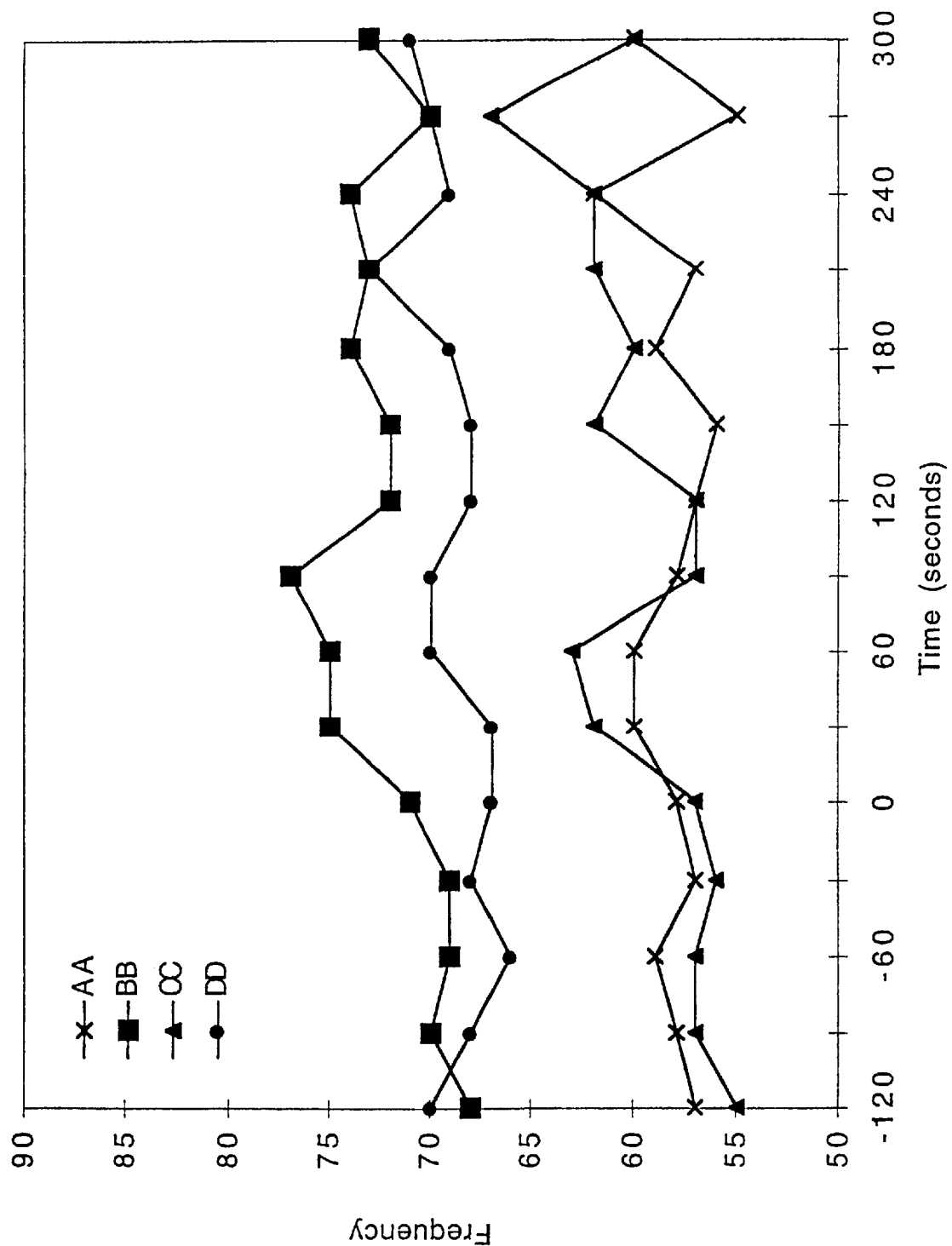

FIG. 3 shows the influence of application of Nicorette® 4 mg chewing gum on the heart beat frequency (rate) of four individuals (AA, BB, CC, and DD) as a function of time. Time –120—0 represents time prior to application of the dosage form. At time 0 individuals applied the buccal tablet according to the test protocol.

DETAILED DESCRIPTION OF THE INVENTION

It is the primary object of the present invention to provide a tobacco supplement or a tobacco substitute, for use in e.g. smoking cessation and nicotine replacement therapies which provide the user with a satisfactory dose of nicotine so as to reduce tobacco withdrawal symptoms without causing an unacceptable local irritation. More specifically it is the object of the invention to provide such a nicotine containing tablet, for transmucosal, preferably buccal, delivery, which disintegrates and/or melts at body temperature with or without the aid of salivary fluid or mechanical erosion, or a combination thereof after which the formulation shows adhesiveness towards the body tissue in the oral cavity.

Further objects of the invention will become apparent to one skilled in the art, and still other objects will become apparent hereinafter.

According to the invention nicotine is provided in an apolar-polar vehicle chiefly comprising fat, carbohydrate and/or polyols, and a surface-active substance.

Pharmaceutically acceptable apolar components according to the invention include in the broadest sense of the invention any lipid (oil, fat, or wax) such as cocoa butter and cocoa butter alternatives (including cocoa butter equivalents (CBE), cocoa butter substitutes (CBS), cocoa butter replacers (CBR), cocoa butter improvers (CBI) (Minifie, B. Chocolate, Cocoa, and Confectionery: Science and Technology, $2^{nd}$ ed, 1980, p 80–88. AVI Publ. Comp., Inc, Westport, Conn., USA and in G. Talbot, Vegetable fate, In S. T. Beckett (Ed): Industrial Chocolate Manufacture and Use, $2^{nd}$ ed., 1994, p 242–257, Chapman & Hall, London), coconut, palmkernel oil, and other similar oils characterized by being predominantly based on lauric and myristic acids, corn oil, sunflower oil, hybrid sunflower oil, soybean oil, rapeseed oil, canola oil, olive oil, ricebran oil, cottonseed oil, arachis (peanut, groundnut) oil and other oils characterized by primarily being based on oleic, linoleic and linolenic acids and hydrogenated to a suitable melting point, fish oil, tallow, lard, butterfat, and other animal derived fats, and synthetic fats, reesterified fats, hard fats obtained by a chemical reaction of fatty acids with glycerol using no acidic, alkaline or enzyme catalysis.

The above mentioned fats can be used as single components or mixed with each other; they can be either crude or refined using physical or alkaline refining. They can also be subjected to further processing including catalytic hydrogenation, interesterification, transesterification and fractionation.

Preferably said apolar components produce alone or in mixture with other components of the invention, a formulation of the invention which exhibit a melting point ranging from about 25° C. to about 45° C., preferably from about 33° C. to about 45° C. with or without the addition of polar solvent or body fluid such as salivary fluid.

Especially useful are edible and pharmaceutically acceptable vegetable fats with a fatty acid composition chiefly being based on C14:0, C16:0, C18:0, C18:1 and C18:2, most useful those being rich in C16 and C18, and any combination thereof having melting point ranging between from about 25° C. to about 45° C., preferably from about 30° C. to about 45° C. Especially preferable are vegetable fats in particular, tempering or non-tempering fats including CBA's including CBE's, CBR's, CBS's and CBI's known to those skilled in the art which in formulation with other components of the invention exhibit a disintegration time at body temperature, with or without the addition of polar solvent or body fluid such as salivary fluid, which is less than 45 minutes, preferably less than 10 minutes.

Pharmaceutically acceptable carbohydrates as components according to the invention include sucrose, fructose, glucose, galactose and invert sugar.

Pharmaceutically acceptable polyols as components according to the invention include sugar alcohols and mixtures thereof, e.g. xylitol, sorbitol, maltitol, mannitol, isomalt and glycerol. It is readily appreciated by those skilled in the art that synthetic polymers of sugar alcohols and/or carbohydrates, such as polydextrose can comprise in whole or in part the polar component of the invention.

Pharmaceutically acceptable surface-active agents as components of the invention include nonionic, ionic, preferable anionic, and zwittterionic surfactants or mixtures, fractions or derivatives thereof.

Suitable compounds in the group of nonionic surface-active agents include poloxamers, polyoxyethylene alkyl ethers, polyoxyethylene castor oil derivatives, polyoxyethylene sorbitan fatty acid esters, mono- and diglycerides and esters thereof other than specifically mentioned, polyoxyethylene stearates, polyglycerolesters of fatty acids (including polyglycerolpolyricinoleic acid (PGPR)), and sorbitan fatty acid esters.

Anionic surface-active agents as components of the invention include fatty acids and their soaps, lactylates, especially sodium and/or calcium stearoyllactylate, sodium lauryl sulfate, and latanol.

Suitable compounds in the group of zwitterionic surface-active agents include zwitterionic phospholipids, such as phosphatidylcholine and phosphatidylethanolamine. Most preferable are edible pharmaceutically acceptable mixtures of surface-active agents such as soyalecithin and/or egg lecithin and fractions or derivatives thereof As realized by those skilled in the art compatible combinations of surface-active agents are included without departing from the spirit of the invention.

Furthermore, as readily appreciated by those skilled in the art, additives for controlling the behavior of the melting point range, texture, integrity, consistency and moulding properties of the formulation can be incorporated in the invention without departing from the spirit of the invention. It is also readily appreciated by those skilled in the art that thickening agents and agents added to increase colloidal stability are incorporated in the invention.

In addition usually employed pharmaceutical excipients and/or food additives such as flavoring agents, buffering agents, preservatives and such components can be added without departing from the spirit and scope of the invention.

It is, furthermore, appreciated by those skilled in the art that conventional variations of product design such as tablets being solid moulded with center filling or center additions, drops, and coated variations thereof fall within the scope of the invention.

It is, furthermore, appreciated by those skilled in the art that the method of manufacturing depends chiefly on the choice of apolar and polar composition. Therefore variations of methods of manufacturing of the invention and equipment used therefore falls within the scope of the invention. This includes methods and processes of temperature treatment and techniques for particle size reduction.

The embodiments, practice and methods of manufacturing the compositions of this invention is further illustrated by the following non-limiting examples:

EXAMPLE 1

CBR Bases

The influence of nicotine on the melting point range of commercially available cocoa butter replacers was determined using differential scanning calorimetry (DSC Perkin Elmer with scanning rate at 2.5° C.). Analyses were performed on samples containing four different CBR's (Akopol E, Akoprime E (a hydrogenated vegetable oil type II NF 18), Akomel S and Akocote RT, all of Karlshamns Sweden AB) with melting point (mp °C.) and fatty acid composition according to the manufacturer—see below Table 1.

TABLE 1

| CBR | Mp ° C. | Fatty acid composition | | | | | |
|---|---|---|---|---|---|---|---|
| | | C12:0 | C14:0 | C16:0 | C18:0 | C18:1 | C18:2 |
| Akopol E | 34 | 0.2 | 0.4 | 17.5 | 11.5 | 65.0 | 4.0 |
| Akoprime E | 34 | 0.2 | 0.5 | 20.0 | 10.0 | 65.0 | 4.0 |
| Akomel S | 34 | 0.2 | 0.5 | 21.0 | 8.5 | 63.4 | 4.6 |
| Akocote RT | 38.5 | 0.1 | 0.5 | 20.0 | 7.0 | 65.5 | 4.5 |

To the CBR's were added different amounts of nicotine (0, 1, 2, 4 and 6 mg/g). Additional analyses were performed on Akomel S with 12 mg/g nicotine.

No significant difference in onset temperature and peak temperature for any of the CBR's at any of the levels of nicotine was observed as compared to those stated by the manufacturer and as compared to samples without nicotine addition. This indicates that the melting point range of the CBR's is not significantly influenced by the addition of nicotine.

One week storage at 5° C., 20° C. and 30° C. of Akopol E with 2 mg/g nicotine does not significantly influence the melting point range as indicated by the onset and peak temperature determined by DSC. Similar results were obtained with Akoprime E with 2 mg/g nicotine analyzed after temperature cycling (5° C.–40° C., 40° C.–5° C.).

Formulations containing 2 mg/g nicotine in mixtures of 90.7 Akoprime E and 9.1 weight % lecithin (Epicuron® 200, Lucas Meyer, Germany), did not show any significant difference in melting point range as compared to 0 mg/g nicotine level. Addition of lecithin caused a significantly reduced variation between samples. Addition of 10 weight % sucrose or 10 weight % xylitol and with concentrations of 1–6 mg/g nicotine did not show any significant difference in melting point range as compared to 0 mg/g nicotine level.

EXAMPLE 2
Fatty Base Witepsol®

50 g of commercially available suppository base Witepsol® H15 (Hüls AG, Germany) with an open-tube melting point range of 33.5° C.–35.5° C. was melted. Portions of 0.5 g were moulded in blisters made of a copolymer of acrylonitrile and methyl acrylate (Barex®) and cooled. 2 or 4 mg pure nicotine was added to each blister whereafter an additional amount of 0.4 g of melted fatty base was added.

EXAMPLE 3
Cocoa Butter Base

Batches of 20, 30, 35 and 40 g respectively of cocoa butter were melted and kept at 40° C. To the melts 10, 15, 20 and 30 g respectively of icing sugar was added whereafter the melts were homogenized. Subsequently, 0.125 mg of pure nicotine was added to each batch. Pieces of 0.8 g from the melts were moulded in blisters.

Below Examples 4–17 discloses manufacturing of formulations according to the present invention. Examples 4–9 represent formulations with a relatively high percentage of lipids, while Examples 10–17 represent formulations with a relatively low percentage of lipids.

When manufacturing according to Examples 4–17 is transferred to large-scale production the manufacturing need be adopted using state-of-the art technology. Basically the following procedure is thereby used.

A part of the lipid is melted. The solid components are added and mixed. A reduction of particle size of the solid components is performed by milling in a roll-refiner. If the solid components have already got the required particle size, e g by milling before the mixing with the lipid, roll-refining is dispensed with. After treatment in the roll-refiner the mixture is remelted and mixed with the rest of the lipid, which is also melted. A mixing of the melt, so called conching, is performed in a suitable mixer. Emulsifier and nicotine is added. Tablets or other solid dosage forms are subsequently made using suitable techniques, such as moulding, extrusion, congealing, including pastillation, or compacting, when necessary after suitable preconditioning.

EXAMPLE 4

Apolar (Akoprime E) and polar (xylitol) components of the invention were mixed according to the composition of the below Table 2.

TABLE 2

| Component: | Weight %: |
|---|---|
| Akoprime E | 84.5 |
| Xylitol | 10.0 |
| Nicotine free base | 0.5 |
| Egg lecithin (purified egg phospholipids) | 5.0 |

Dosage forms with this composition were produced by melting Akoprime E at 40° C. until a clear solution phase was obtained. At 40° C. xylitol was added in portions and under homogenization until a visually dispersed system was obtained after which nicotine was added. At 40° C. the mixture was further homogenized after which lecithin was added under continued homogenization. The so obtained mixture was dispensed and moulded in blisters and cooled to room temperature resulting in pieces of 0.8 g.

EXAMPLE 5

Apolar (Akoprime E) and polar (xylitol) components of the invention were mixed according to the composition of below Table 3.

TABLE 3

| Component: | Weight %: |
|---|---|
| Akoprime E | 67.6 |
| Cacao | 16.9 |
| Xylitol | 10.0 |
| Nicotine free base | 0.5 |
| Egg lecithin (purified egg phospholipids) | 5.0 |

Dosage forms with this composition were produced by melting Akoprime E at 40° C. until a clear solution phase was obtained. At 40° C. xylitol and cacao, a flavoring agent, were added in portions and under homogenization until a visually dispersed system was obtained after which nicotine was added. At 40° C. the mixture was further homogenized after which lecithin was added under continued homogenization. The so obtained mixture was dispensed and moulded in blisters and cooled to room temperature resulting in pieces of 0.8 g.

EXAMPLE 6

In essentially the same way as in Example 4 and 5 the below composition was manufactured according to Table 4.

TABLE 4

| Component: | Weight %: |
|---|---|
| Akoprime E | 79.5 |
| Xylitol | 10.0 |
| Nicotine free base | 0.5 |
| Egg lecithin (purified egg phospholipids) | 10.0 |

EXAMPLE 7

In essentially the same way as in Example 4 and 5 the below composition was manufactured according to Table 5.

TABLE 5

| Component: | Weight %: |
|---|---|
| Akoprime E | 77.3 |
| Xylitol | 10.0 |
| Nicotine resin complex | 2.7 |
| Egg lecithin (purified egg phospholipids) | 10.0 |

EXAMPLE 8

In essentially the same way as in Example 4 and 5 the below composition was manufactured according to Table 6.

TABLE 6

| Component: | Weight %: |
|---|---|
| Akoprime E | 75.7 |
| Xylitol | 10.0 |
| Nicotine β-cyclodextrin complex | 4.3 |
| Egg lecithin (purified egg phospholipids) | 10.0 |

EXAMPLE 9

In essentially the same way as in Example 4 and 5 the below composition was manufactured according to Table 7.

TABLE 7

| Component: | Weight %: |
| --- | --- |
| Akoprime E | 78.5 |
| Xylitol | 10.0 |
| Nicotine hydrogen tartrate | 1.5 |
| Egg lecithin (purified egg phospholipids) | 10.0 |

EXAMPLE 10

Apolar (Akosol 37) and polar (xylitol) components of the invention were mixed according to the composition of the below Table 8. Akosol 37 is a hydrogenated palm oil of Karlshamns Sweden AB.

TABLE 8

| Component: | Weight %: |
| --- | --- |
| Akosol 37 | 33.9 |
| Xylitol | 45.0 |
| Corn starch | 20.0 |
| Nicotine free base | 0.4 |
| Egg lecithin (purified egg phospholipids) | 0.7 |

Akosol 37 was melted at 70° C. and lecithin was added under homogenization. A mixture of xylitol and cornstarch was added and homogenized. The role of the cornstarch was to act as filler. Finally nicotine was added and homogenized. The mixture was moulded and cooled. The moulds were of size 0.75 g or 1.29 g.

EXAMPLE 11

In essentially the same way as in Example 10 the following composition was manufactured according to below Table 9.

TABLE 9

| Component: | Weight %: |
| --- | --- |
| Akosol 37 | 31.0 |
| Xylitol | 45.0 |
| Corn starch | 19.9 |
| Nicotine free base | 0.4 |
| Egg lecithin (purified egg phospholipids) | 0.7 |
| Sodium carbonate | 3.0 |

The sodium carbonate was added together with the mixture of xylitol and cornstarch. The role of the sodium carbonate was to act as a buffer for increasing bioavailability.

EXAMPLE 12

In essentially the same way as in Example 10 the following composition was manufactured according to below Table 10.

TABLE 10

| Component: | Weight %: |
| --- | --- |
| Akosol 37 | 31.8 |
| Xylitol | 45.0 |
| Corn starch | 20.0 |
| Nicotine β-cyclodextrin complex | 2.5 |
| Egg lecithin (purified egg phospholipids) | 0.7 |

The nicotine β-cyclodextrin complex was added after the addition of xylitol and cornstarch.

EXAMPLE 13

In essentially the same way as in Example 10 the following composition was manufactured according to below Table 11.

TABLE 11

| Component: | Weight %: |
| --- | --- |
| Akosol 37 | 29.5 |
| Xylitol | 45.0 |
| Corn starch | 20.0 |
| Sodium carbonate | 2.3 |
| Nicotine β-cyclodextrin complex | 2.6 |
| Egg lecithin (purified egg phospholipids) | 0.6 |

The nicotine β-cyclodextrin complex was added after the addition of xylitol, cornstarch and sodium carbonate.

EXAMPLE 14

In essentially the same way as in Example 10 the following composition was manufactured according to below Table 12.

TABLE 12

| Component: | Weight %: |
| --- | --- |
| Akosol 37 | 32.7 |
| Xylitol | 45.0 |
| Corn starch | 20.0 |
| Nicotine resin complex | 1.7 |
| Egg lecithin (purified egg phospholipids) | 0.6 |

The nicotine resin complex was added after the addition of xylitol and cornstarch.

EXAMPLE 15

In essentially the same way as in Example 10 the following composition was manufactured according to below Table 13.

TABLE 13

| Component: | Weight %: |
| --- | --- |
| Akosol 37 | 30.4 |
| Xylitol | 45.0 |
| Corn starch | 20.0 |
| Sodium carbonate | 2.3 |

TABLE 13-continued

| Component: | Weight %: |
|---|---|
| Nicotine resin complex | 1.7 |
| Egg lecithin (purified egg phospholipids) | 0.6 |

The nicotine resin complex was added after the addition of xylitol, cornstarch and sodium carbonate.

EXAMPLE 16

In essentially the same way as in Example 10 the following composition was manufactured according to below Table 14.

TABLE 14

| Component: | Weight %: |
|---|---|
| Akosol 37 | 33.5 |
| Xylitol | 45.0 |
| Corn starch | 20.0 |
| Nicotine hydrogen tartrate | 0.9 |
| Egg lecithin (purified egg phospholipids) | 0.6 |

The nicotine hydrogen tartrate was added after the addition of xylitol and cornstarch.

EXAMPLE 17

In essentially the same way as in Example 10 the following composition was manufactured according to Table 15.

TABLE 14

| Component: | Weight %: |
|---|---|
| Akosol 37 | 31.2 |
| Xylitol | 45.0 |
| Corn starch | 20.0 |
| Sodium carbonate | 2.3 |
| Nicotine hydrogen tartrate | 0.9 |
| Egg lecithin (purified egg phospholipids) | 0.6 |

The nicotine resin complex was added after the addition of xylitol, cornstarch and sodium carbonate.

EXAMPLE 18

Buccal tablets according to Examples 4 and 5 were tested on humans.
Experimental Design
Test Subjects
  Subjects: healthy male volunteers; ages 32–55.
  Number of test subjects: 4.
  Study identification of test subjects: AA, BB, CC, and DD.
Test System
  Two formulations of the invention with composition according to Examples 4 and 5 were tested.
Reference System
  Commercially available Nicorette® 4 mg chewing gum (Pharmacia & Upjohn).
Application
  For the purpose of controlling the site of application and thus the disintegration (melting, erosion, dissolution etc.) of the dosage form according to the invention (Examples 4 and 5), the test subjects were to apply it to the inside of the cheek. The test subjects were allowed to change position of the dosage form at any time as long as the major residence time occurred at the inside of the cheek. The test subjects were also allowed to swallow at wish. Application and usage of Nicorette® 4 mg chewing gum followed recommendations issued by the manufacturer (Pharmacia & Upjohn). For the purpose of clarity the test subjects were also in the study of the reference system allowed to swallow at wish.
Test Protocol
  The order of application of the two test systems and the reference system was randomized for each test subject. The test subjects were seated during all studies. The test subjects' heart beat frequency was monitored with readings every 30 sec., starting at minus (–) 120 seconds prior to application (time zero, 0) of the current dosage form (frequency at rest) and continuing thereafter for 300 sec. See FIGS. 1–3. After each application the test subjects had again to reach frequency at rest prior to a new application. A minimum of 15 minutes of rest was, however, required. Each test was performed in single dose.
Results
  Frequency at rest was expressed as the geometric mean value of the frequency obtained between time (–) 120 seconds prior to application and time (–) 30 seconds prior to application. A geometric mean value of the frequency obtained after application was expressed as the mean frequency obtained between time 210–300 seconds after application. The difference between frequency after application and frequency at rest expresses an average increase of the frequency due to the application of the invention.
  Results according to the below Table 16 were obtained.

TABLE 16

| | Test Subjects | | | |
|---|---|---|---|---|
| | AA | BB | CC | DD |
| Application of Example 4 | | | | |
| Frequency at rest (PAR) | 61,50 | 67,75 | 57,75 | 71,25 |
| Frequency after application (PAA) | 67,50 | 75,25 | 65,50 | 79,75 |
| PAA-PAR | 6,00 | 7,50 | 7,75 | 8,50 |
| Average increase of frequency | 7,4 | | | |
| Application of Example 5 | | | | |
| Frequency at rest (PAR) | 58,50 | 63,00 | 57,75 | 67,75 |
| Frequency after application (PAA) | 58,75 | 76,75 | 62,50 | 75,25 |
| PAA-PAR | 0,25 | 13,75 | 4,75 | 7,50 |
| Average increase of frequency | 6,6 | | | |
| Application of Nicorette ® 4 mg chewing gum | | | | |
| Frequency at rest (PAR) | 57,75 | 69,00 | 56,25 | 68,00 |
| Frequency after application (PAA) | 58,50 | 72,50 | 62,75 | 70,75 |
| PAA-PAR | 0,75 | 3,50 | 6,50 | 2,75 |
| Average increase of frequency | 3,4 | | | |

Comparison between application of Examples 4 and 5 and application of Nicorette® 4 mg chewing gum using the average increase of frequency of all test subjects in each application shows a significantly higher increase of frequency due to application of Examples 4 and 5 of the invention as compared to application of Nicorette® 4 mg chewing gum. None of the test subjects reported any local irritation beyond that experienced with Nicorette® 4 mg chewing gum.

The compositions according to the present invention are primarily intended to be an only formulation to be administered during nicotine replacement therapy (NRT). Anyhow it is fully possible during NRT to administer nicotine using the present compositions concomitantly or in combination with administration of nicotine through other routes. One suitable such other route is a device for transdermal administration of nicotine, one example of which is the Nicorette® Nicotine Patch.

What is claimed is:

1. A nicotine-containing pharmaceutical composition being devoid of polyethylene glycol, comprising one or more cocoa butter or cocoa butter alternatives present in the amount of 5%–90% by weight, one or more polar components present in the amount of 1%–70% by weight, and one or more surface-active components present in the amount of 0.01%–30% by weight, and optionally pharmacologically acceptable excipients, and wherein said composition provides transmucosal absorption of nicotine.

2. A nicotine-containing pharmaceutical composition being devoid of polyethylene glycol, comprising one or more apolar components selected from the group consisting of oils based on lauric and myristic acids, oils based on palmitic, oleic, and stearic acids, oils based on oleic, linoleic and linolenic acids, and oils based on animal fat in the amount of 5%–90% by weight, one or more polar components present in the amount of 1%–70% by weight, and one or more surface-active components present in the amount of 0.01%–30% by weight, and optionally pharmacologically acceptable excipients, and wherein said composition provides transmucosal absorption of nicotine.

3. The composition of claim 2, wherein the oils based on palmitic, oleic and stearic acids are palm oil, shea butter, karite butter, illipe butter, mango kernal oil, or sal fat.

4. The composition of claim 2, wherein the oils based on oleic, linoleic and linolenic acids are corn oil, sunflower oil, hybrid sunflower oil, soybean oil, rapeseed oil, canola oil, olive oil, ricebran oil, cottonseed oil, or arachis oil.

5. The composition of claim 2, wherein the oils based on animal fat are fish oil, tallow, lard, or butterfat.

6. A nicotine-containing pharmaceutical composition being devoid of polyethylene glycol, comprising one or more apolar components selected from the group consisting of synthetic fats, reesterifed fats, and hard fats in the amount of 5%–90% by weight, one or more polar components present in the amount of 1%–70% by weight, and one or more surface-active components present in the amount of 0.01%–30% by weight, and optionally pharmacologically acceptable excipients, and wherein said composition provides transmucosal absorption of nicotine.

7. A nicotine-containing pharmaceutical composition being devoid of polyethylene glycol, comprising one or more cocoa butter replacers present in the amount of 5%–90% by weight, one or more polar components present in the amount of 1%–70% by weight, and one or more surface-active components present in the amount of 0.01%–30% by weight, and optionally pharmacologically acceptable excipients, and wherein said composition provides transmucosal absorption of nicotine.

8. The composition of claim 7, wherein said polar component is selected from the group of polyols consisting of xylitol, sorbitol, maltitol, mannitol, isomalt and glycerol.

9. The composition of claim 7, wherein said polar component is selected from the group of carbohydrates consisting of sucrose, fructose, glucose, galactose, and invert sugar.

10. The composition of claim 8 wherein said polar component is xylitol.

11. A nicotine-containing pharmaceutical composition being devoid of polyethylene glycol, comprising one or more apolar components present in the amount of 5%–90% by weight, one or more polar components present in the amount of 1%–70% by weight, and one or nonionic surfactants selected from the group consisting of poloxamer, polyoxyethylene alkyl ether, polyoxyethylene castor oil derivative, polyoxyethylene sorbitan fatty acid ester; monoglyceride, diglyceride and esther, polyoxyethylene stearate, polyglycerolester of fatty acids, and sorbitan fatty acid ester present in the amount of 0.01%–30% by weight, and optionally pharmacologically acceptable excipients, and wherein said composition provides transmucosal absorption of nicotine.

12. A nicotine-containing pharmaceutical composition being devoid of polyethylene glycol, comprising one or more apolar components present in the amount of 5%–90% by weight, one or more polar components present in the amount of 1%–70% by weight, and one or more anionic surfactant agents selected from the group consisting of fatty acid, soap of fatty acid, lactylate, sodium stearoyllactylate, calcium stearoyllactylate, sodium lauryl sulfate, and latanol present in the amount of 0.01%–30% by weight, and optionally pharmacologically acceptable excipients, and wherein said composition provides transmucosal absorption of nicotine.

13. The composition of claim 12 further comprising filler and a buffering agent.

14. The composition of claim 12 further comprising a buffering agent.

15. The composition of claim 12, wherein the nicotine is present as a free base, a resin complex, a cyclodextrin complex or a salt or mixtures thereof.

16. The composition of claim 15, wherein said salt is hydrogen tartrate.

17. The composition of claim 15, wherein said composition is formulated having a dosage form from about 1 mg to 10 mg of nicotine.

18. The composition of claim 17, wherein said composition is administered to a person by an oral cavity.

19. The composition of claim 18, wherein said dosage form disintegrates in the oral cavity in less than 45 minutes after application therein.

20. The composition of claim 18, wherein said dosage form disintegrates in the oral cavity in less than 10 minutes after application therein.

21. The composition of claim 15, wherein said composition is administered to a person by a buccal delivery.

22. The composition of claim 15, wherein said composition is administered to a person by a transmucosal delivery.

23. The composition of claim 1 wherein said apolar, polar and surface-active components are present in amounts of 25%–85%, 5%–50% and 0.5%–15% by weight respectively.

24. The composition of claim 2 wherein said apolar, polar and surface-active components are present in amounts of 25%–85%, 5%–50% and 0.5%–15% by weight respectively.

25. The composition of claim 1, wherein the cocoa butter alternatives are selected from the group consisting of cocoa butter equivalents, cocoa butter substitutes, cocoa butter replacers, and cocoa butter improvers.

26. The composition of claim 2 wherein the oils based on lauric and myristic acids are coconut oil or palmkernel oil.

27. The composition of claim 1, wherein said polar component is selected from the group of polyols consisting of xylitol, sorbitol, maltitol, mannitol, isomalt and glycerol.

28. The composition of claim 22 wherein said polar component is xylitol.

29. The composition of claim 1, wherein said polar component is selected from the group of carbohydrates consisting of sucrose, fructose, glucose, galactose, and invert sugar.

30. The composition of claim 2, wherein said polar component is selected from the group of polyols consisting of xylitol, sorbitol, maltitol, mannitol, isomalt and glycerol.

31. The composition of claim 30 wherein said polar component is xylitol.

32. The composition of claim 2, wherein said polar component is selected from the group of carbohydrates consisting of sucrose, fructose, glucose, galactose, and invert sugar.

33. The composition of claim 6, wherein said polar component is selected from the group of polyols consisting of xylitol, sorbitol, maltitol, mannitol, isomalt and glycerol.

34. The composition of claim 33 wherein said polar component is xylitol.

35. The composition of claim 6, wherein said polar component is selected from the group of carbohydrates consisting of sucrose, fructose, glucose, galactose, and invert sugar.

36. The composition of claim 1 further comprising filler and a buffering agent.

37. The composition of claim 1 further comprising a buffering agent.

38. The composition of claim 1, wherein the nicotine is present as a free base, a resin complex, a cyclodextrin complex or a salt or mixtures thereof.

39. The composition of claim 38, wherein said salt is hydrogen tartrate.

40. The composition of claim 38, wherein said composition is formulated having a dosage form from about 1 mg to 10 mg of nicotine.

41. The composition of claim 40, wherein said composition is administered to a person by an oral cavity.

42. The composition of claim 41, wherein said dosage form disintegrates in the oral cavity in less than 45 minutes after application therein.

43. The composition of claim 41, wherein said dosage form disintegrates in the oral cavity in less than 10 minutes after application therein.

44. The composition of claim 38, wherein said composition is administered to a person by a buccal delivery.

45. The composition of claim 38, wherein said composition is administered to a person by a transmucosal delivery.

46. The composition of claim 2 further comprising filler and a buffering agent.

47. The composition of claim 2 further comprising a buffering agent.

48. The composition of claim 2, wherein the nicotine is present as a free base, a resin complex, a cyclodextrin complex or a salt or mixtures thereof.

49. The composition of claim 48, wherein said salt is hydrogen tartrate.

50. The composition of claim 48, wherein said composition is formulated having a dosage form from about 1 mg to 10 mg of nicotine.

51. The composition of claim 50, wherein said composition is administered to a person by an oral cavity.

52. The composition of claim 51, wherein said dosage form disintegrates in the oral cavity in less than 45 minutes after application therein.

53. The composition of claim 51, wherein said dosage form disintegrates in the oral cavity in less than 10 minutes after application therein.

54. The composition of claim 48, wherein said composition is administered to a person by a buccal delivery.

55. The composition of claim 48, wherein said composition is administered to a person by a transmucosal delivery.

56. The composition of claim 6 further comprising filler and a buffering agent.

57. The composition of claim 6 further comprising a buffering agent.

58. The composition of claim 6, wherein the nicotine is present as a free base, a resin complex, a cyclodextrin complex or a salt or mixtures thereof.

59. The composition of claim 58, wherein said salt is hydrogen tartrate.

60. The composition of claim 58, wherein said composition is formulated having a dosage form from about 1 mg to 10 mg of nicotine.

61. The composition of claim 60, wherein said composition is administered to a person by an oral cavity.

62. The composition of claim 61, wherein said dosage form disintegrates in the oral cavity in less than 45 minutes after application therein.

63. The composition of claim 61, wherein said dosage form disintegrates in the oral cavity in less than 10 minutes after application therein.

64. The composition of claim 58, wherein said composition is administered to a person by a buccal delivery.

65. The composition of claim 58, wherein said composition is administered to a person by a transmucosal delivery.

66. The composition of claim 7 further comprising filler and a buffering agent.

67. The composition of claim 7 further comprising a buffering agent.

68. The composition of claim 7, wherein the nicotine is present as a free base, a resin complex, a cyclodextrin complex or a salt or mixtures thereof.

69. The composition of claim 68, wherein said salt is hydrogen tartrate.

70. The composition of claim 68, wherein said composition is formulated having a dosage form from about 1 mg to 10 mg of nicotine.

71. The composition of claim 70, wherein said composition is administered to a person by an oral cavity.

72. The composition of claim 71, wherein said dosage form disintegrates in the oral cavity in less than 45 minutes after application therein.

73. The composition of claim 71, wherein said dosage form disintegrates in the oral cavity in less than 10 minutes after application therein.

74. The composition of claim 68, wherein said composition is administered to a person by a buccal delivery.

75. The composition of claim 68, wherein said composition is administered to a person by a transmucosal delivery.

76. The composition of claim 11, further comprising filler and a buffering agent.

77. The composition of claim 11 further comprising a buffering agent.

78. The composition of claim 11, wherein the nicotine is present as a free base, a resin complex, a cyclodextrin complex or a salt or mixtures thereof.

79. The composition of claim 78, wherein said salt is hydrogen tartrate.

80. The composition of claim 78, wherein said composition is formulated having a dosage form from about 1 mg to 10 mg of nicotine.

81. The composition of claim 80, wherein said composition is administered to a person by an oral cavity.

82. The composition of claim 81, wherein said dosage form disintegrates in the oral cavity in less than 45 minutes after application therein.

83. The composition of claim 81, wherein said dosage form disintegrates in the oral cavity in less than 10 minutes after application therein.

84. The composition of claim 78, wherein said composition is administered to a person by a buccal delivery.

85. The composition of claim 78, wherein said composition is administered to a person by a transmucosal delivery.

86. The composition of claim 6 wherein said apolar, polar and surface-active components are present in amounts of 25%–85%, 5%–50% and 0.5%–15% by weight respectively.

87. The composition of claim 7, wherein said apolar and surface-active components are present in amounts of 25%–85%, 5%–50% and 0.5%–15% by weight respectively.

88. The composition of claim 11 wherein said apolar, polar and surface-active components are present in amounts of 25%–85%, 5%–50% and 0.5%–15% by weight respectively.

89. The composition of claim 12, wherein said apolar, polar and surface-active components are present in amounts of 25%–85%, 5%–50% and 0.5%–15% by weight respectively.

* * * * *